United States Patent [19]

Bartlett

[11] Patent Number: 5,441,502
[45] Date of Patent: Aug. 15, 1995

[54] SYSTEM AND METHOD FOR RE-ATTACHING SOFT TISSUE TO BONE

[75] Inventor: Edwin C. Bartlett, Greenville, N.C.

[73] Assignee: Mitek Surgical Products, Inc., Westwood, Mass.

[21] Appl. No.: 18,929

[22] Filed: Feb. 17, 1993

[51] Int. Cl.⁶ .......................... A61F 5/00; A61B 17/18
[52] U.S. Cl. ...................... 606/104; 606/96; 606/75
[58] Field of Search .............. 606/53, 72–75, 606/80, 81, 96, 102, 104, 139, 232

[56] References Cited

U.S. PATENT DOCUMENTS

| 2,243,717 | 5/1941 | Moreira | 606/104 |
|---|---|---|---|
| 2,243,718 | 5/1941 | Moreira | 606/80 |
| 2,267,925 | 12/1941 | Johnston | 606/104 |
| 3,848,601 | 11/1974 | Ma et al. | 606/80 |
| 3,892,232 | 7/1975 | Neufeld | 606/73 |
| 4,537,185 | 8/1985 | Stednitz | 606/73 |
| 4,738,255 | 4/1988 | Goble et al. | 606/232 |
| 5,197,967 | 3/1993 | Wilson | 606/80 |
| 5,203,784 | 4/1993 | Ross et al. | 606/72 |
| 5,250,055 | 10/1993 | Moore et al. | 606/96 |
| 5,261,914 | 11/1993 | Warren | 606/73 |

FOREIGN PATENT DOCUMENTS 0643131  5/1984  Switzerland ............... 606/73

*Primary Examiner*—Stephen C. Pellegrino
*Assistant Examiner*—Nancy Mulcare
*Attorney, Agent, or Firm*—Pandiscio & Pandiscio

[57] ABSTRACT

A system and method for re-attaching soft tissue to bone. In its preferred embodiment, the system comprises pin means, sleeve means, driver means, suture anchor means and suture anchor installation tool means. In use, the soft tissue is placed against the surface of the bone in its desired re-attachment position. Then the pin means is passed through the soft tissue and into the bone to securely fix the pin means (and hence the soft tissue) to the bone. Then the patient's anatomy is manipulated as needed to determine if the soft tissue has been properly positioned relative to the bone. If the soft tissue is properly positioned, the surgeon proceeds to the next step in the procedure; if not, the pin means is removed and the tissue positioning operation repeated until the soft tissue has been positioned in the desired location. Next, the sleeve means is slid telescopically over the pin means, passed through the soft tissue and then, using the driver means, drilled into the bone. Then the pin means is completely withdrawn from the bone and the soft tissue, leaving a hole in the bone. The suture anchor means is then passed down the interior of the sleeve means and into the bone, using the suture anchor installation tool means. Then the installation tool means is withdrawn from the sleeve means, leaving the suture anchor means deployed in the bone and its associated suture extending out through the sleeve means. The sleeve means is then withdrawn, and the free ends of the suture used to secure the soft tissue to the bone.

9 Claims, 11 Drawing Sheets

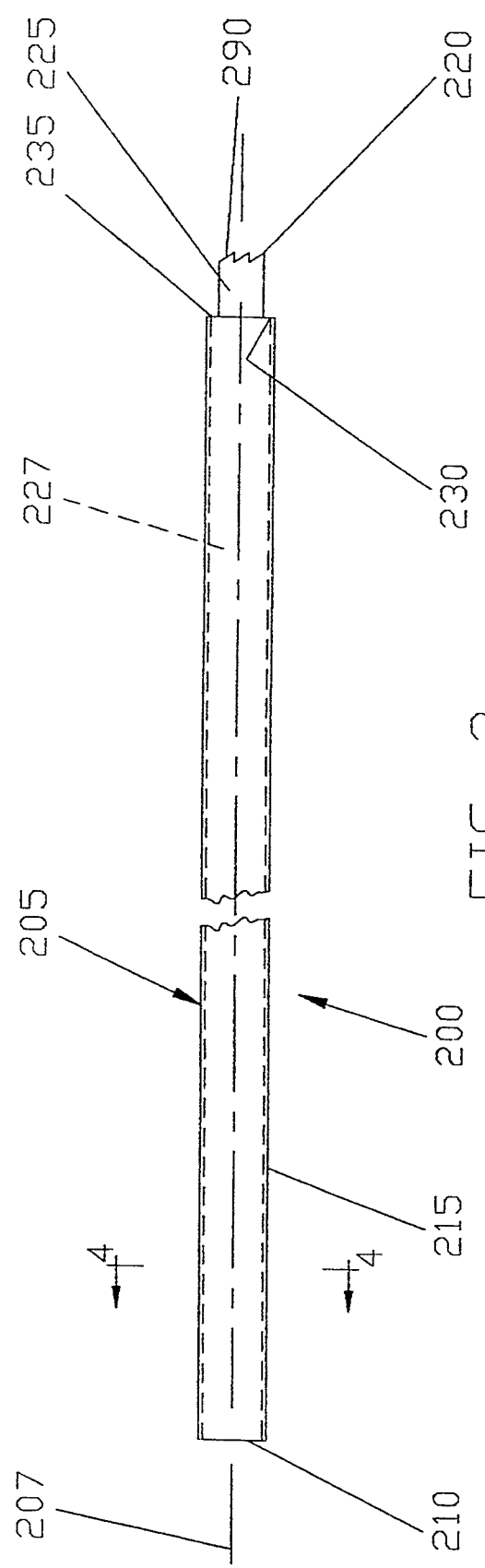

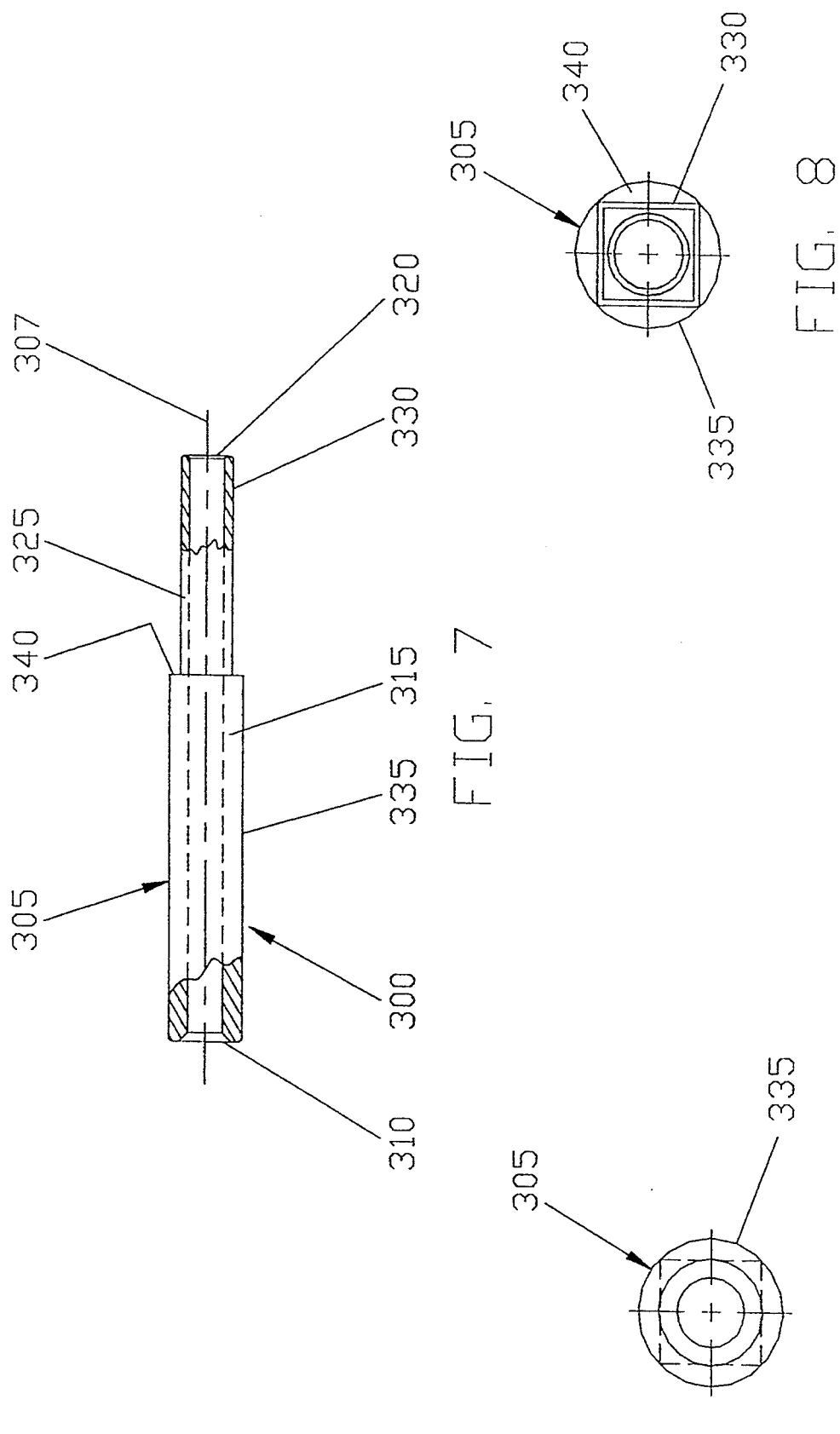

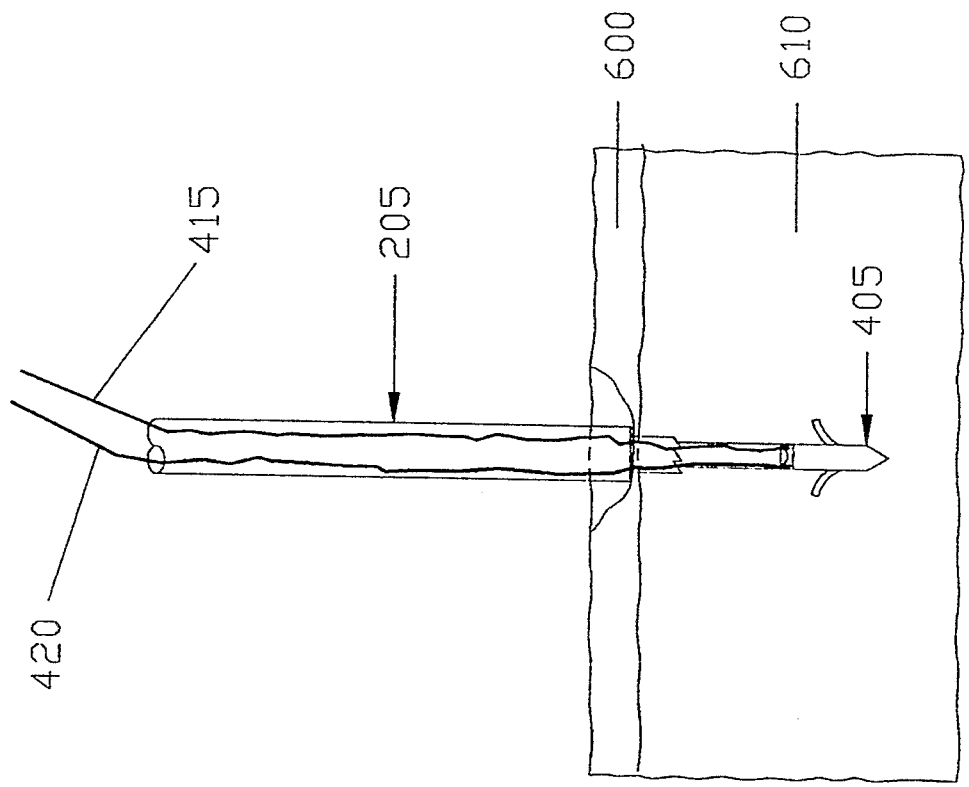
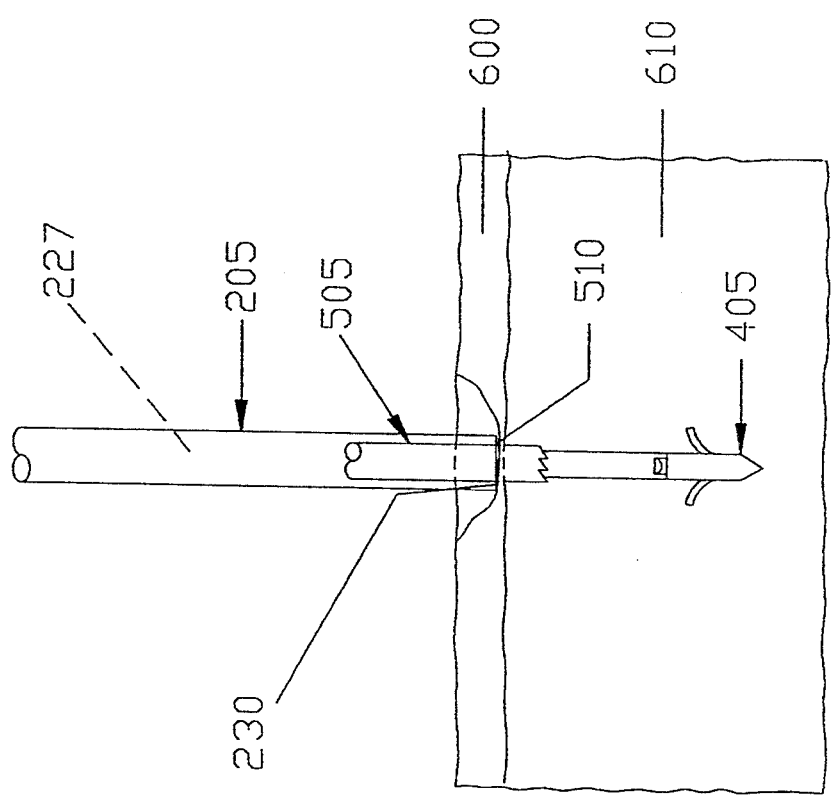
FIG. 18
FIG. 17

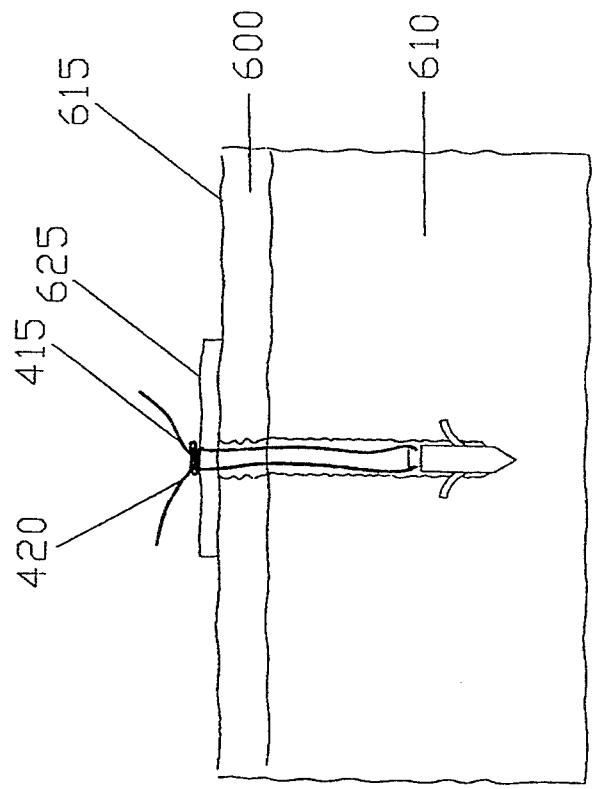
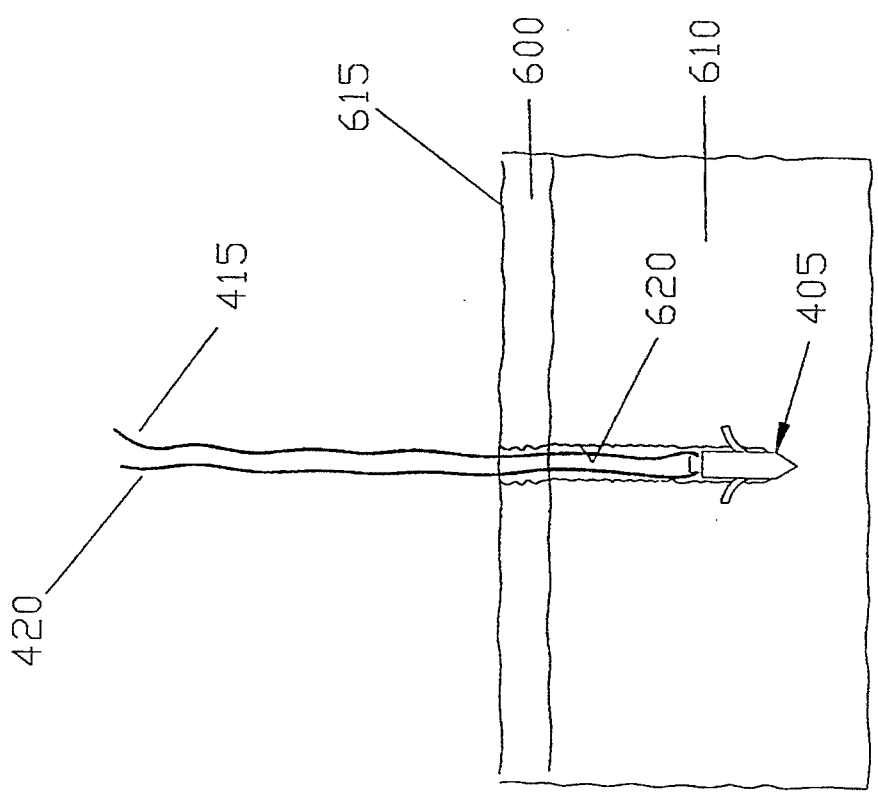

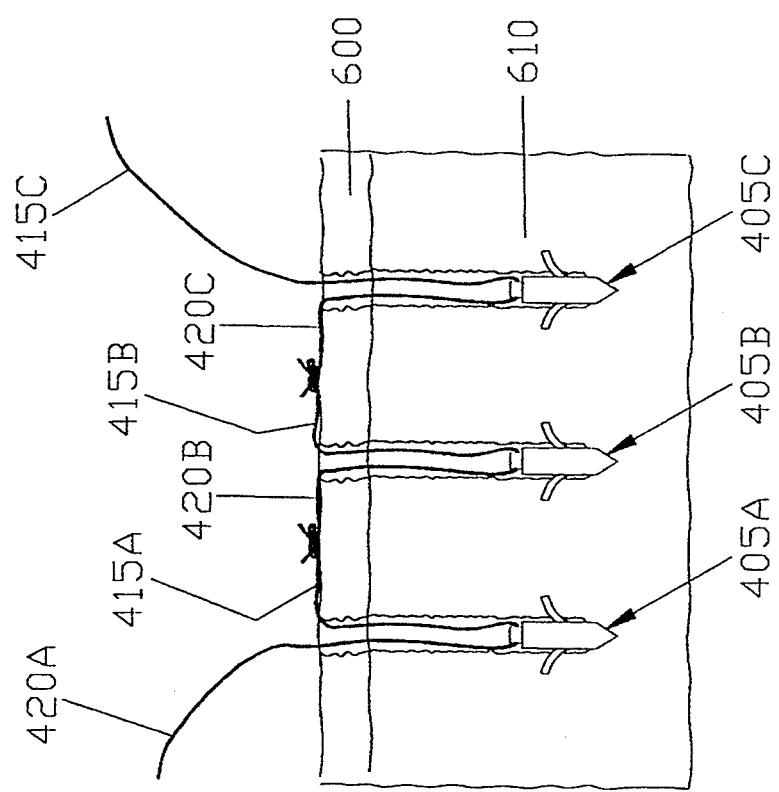

SYSTEM AND METHOD FOR RE-ATTACHING SOFT TISSUE TO BONE

FIELD OF THE INVENTION

This invention relates generally to medical devices and procedures. More particularly, this invention relates to systems amid methods for re-attaching soft tissue to bone.

BACKGROUND OF THE INVENTION

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, commonly referred to under the general term "sprain", the injury will frequently heal itself, if given sufficient time and if care is taken not to expose the injury to further undue stress. In the event that the soft tissue is completely detached from its associated bone or bones, however, surgery may be needed to re-attach the soft tissue to its associated bone or bones.

Numerous devices are currently available to re-attach soft tissue to bone. Examples of such currently-available devices include screws, staples, cement and sutures.

In certain situations, it is desirable to anchor one end of a length of conventional suture in bone so that the other end of the length of suture resides free outside the bone. The free end of the suture can then be used to re-attach soft tissue to the bone. Suture anchors for anchoring one end of a length of conventional suture in bone, and installation tools for deploying the same, are described and illustrated in U.S. Pat. Nos. 4,898,156; 4,899,743; and 4,968,315, which patents are hereby incorporated herein by reference.

Other known suture anchors are adapted to anchor an intermediate portion of a length of conventional suture in bone so that the two opposite ends of the length of suture reside free outside the bone. These two free ends of suture can then be used to re-attach soft tissue to the bone. Suture anchors of this latter type, and installation tools for deploying the same, are described and illustrated in U.S. Pat. Nos. 4,946,468 and 5,002,550 and in pending U.S. patent applications Ser. Nos. 07/902,513 and 07/837,061, which patents and patent applications are also hereby incorporated herein by reference.

Still other suture anchors and suture anchor installation tools are described and illustrated in U. S. Pat. Nos. 4,738,255 and 4,741,330. These latter patents are also hereby incorporated herein by reference.

In soft tissue re-attachment procedures utilizing suture anchors of the types described above, an anchor-receiving hole is generally first drilled in the bone at the desired point of tissue re-attachment. Then a suture anchor is deployed in the hole using an appropriate installation tool. This effectively locks the suture to the bone, with the free end(s) of the suture extending out of the bone. Next, the soft tissue is moved into position over the hole containing the deployed suture anchor. As this is done, the free end(s) of the suture is (are) simultaneously passed through or around the soft tissue, so that the free end(s) of the suture reside(s) on the far side of the soft tissue. Finally, the suture is used to tie the soft tissue securely to the bone.

Alternatively, in some soft tissue re-attachment procedures utilizing suture anchors of the types described above, the soft tissue may first be moved into position over the bone. Then, while the soft tissue lies in position against the bone, a single hole may be drilled through the soft tissue and into the bone. Next, a suture anchor is passed through the soft tissue and deployed in the bone using an appropriate installation tool. This results in the suture anchor being locked to the bone, with the free end(s) of the suture extending out of the bone and through the soft tissue. Finally, the suture is used to tie the soft tissue securely to the bone.

Unfortunately, in many situations it can be difficult for the surgeon to initially precisely identify the optimum point for tissue re-attachment. Frequently the surgeon must initially attach the soft tissue to the bone at his or her best approximation of the optimum re-attachment point. Thereafter, the patient's anatomy must be manipulated through a range of motions by the surgeon. This manipulation allows the surgeon to determine whether the tissue has been re-attached at the optimum location. If the tissue has not been re-attached at the proper location, the point of re-attachment must be relocated before moving forward with the remainder of the surgical procedure.

It will be understood, therefore, that regardless of which of the above-described anchoring procedures is used, the first re-attachment position may frequently have to be abandoned in favor of a more optimally located re-attachment position. This is generally not desirable, for a variety of reasons.

For one thing, it involves forming additional holes in the bone, and deploying additional suture anchors in those holes. At the same time, at least some of the original holes, containing generally irretrievable suture anchors, are ]left totally unused. Furthermore, if the new attachment point is located close to the original attachment point, as is frequently the case, the presence of holes in too close proximity to one another may weaken the integrity of the bone structure itself. This may in turn undermine the secure attachment of a suture anchor to the bone, or force the surgeon to chose a re-attachment point which is something less than optimal.

OBJECTS OF THE INVENTION

Accordingly, one object of the present invention is to provide a novel system and method for re-attaching soft tissue to bone, which improves upon the deficiencies of the prior art devices and techniques discussed above.

Another object of the present invention is to provide a novel system and method for re-attaching soft tissue to bone, wherein suture anchors do not need to be deployed in the bone until after the soft tissue has been securely attached to the bone and its optimum placement confirmed.

A further object of the present invention is to provide a novel system and method for re-attaching soft tissue to bone which allows the surgeon to determine the optimum location for tissue re-attachment prior to anchoring any connective suture to the bone.

Yet another object of the present invention is to provide a novel system and method for re-attaching soft tissue to bone which avoids irretrievably deploying suture anchors in the bone at locations other than the optimum locations for tissue re-attachment.

Still another object of the present invention is to provide a novel system and method for re-attaching soft tissue to bone which is easy to use and perform.

And another object of the present invention is to provide a novel system and method for re-attaching soft tissue to bone which expedites and facilitates the re-attachment procedure.

Yet another object of the present invention is to provide a novel system and method for re-attaching soft tissue to bone which minimizes trauma to the patient during the re-attachment procedure.

Still another object of the present invention is to provide a novel system and method for re-attaching soft tissue to bone which is also usable in the attachment of prosthetic devices and/or grafts of natural and/or synthetic material to bone or bone-like structures.

And another object of the present invention is to provide a novel system and method for re-attaching soft tissue to bone which can be used in both open surgical procedures and in closed surgical procedures (e.g. arthroscopic or endoscopic surgical procedures) where access to the surgical site is provided by one or more cannulas.

SUMMARY OF THE INVENTION

These and other objects of the present invention are achieved by the provision and use of a novel system and method for re-attaching soft tissue to bone.

In its preferred embodiment, the novel system generally comprises pin means, sleeve means, driver means, suture anchor means, and suture anchor installation tool means.

More specifically, in a preferred embodiment of the invention, the pin means generally comprises an elongate, substantially rigid pin having a longitudinal axis, a proximal end, a proximal portion adjacent the proximal end, a distal end, a distal portion adjacent the distal end, and a circumferential groove. The pin has a substantially circular cross-section along most of its length. The distal portion of the pin tapers inwardly so as to form a sharp point at the distal end. The circumferential groove is located in a plane disposed perpendicular to the pin's longitudinal axis. The groove is spaced a predetermined distance back from the distal end of the pin, and separates the proximal portion of the pin from the distal portion of the pin.

The sleeve means generally comprises an elongate sleeve having a longitudinal axis, a proximal end, a proximal portion adjacent the proximal end, a distal end, and a distal portion adjacent the distal end. The sleeve defines a central lumen extending from its proximal end to its distal end. The proximal portion of the sleeve has substantially square inner and outer cross-sections. The distal portion of the sleeve has substantially circular inner and outer cross-sections. The outer diameter of the distal portion of the sleeve is smaller than the outer diameter of the proximal portion of the sleeve. Similarly, the inner diameter of the distal portion of the sleeve is smaller than the inner diameter of the proximal portion of the sleeve. As a result of this construction, inner and outer shoulders are formed at the point where the sleeve's distal and proximal portions join one another.

The distal end of the sleeve is provided with an annular cutting surface. In the preferred embodiment, this cutting surface comprises a series of pointed, generally triangular projections. These projections are arranged in a distally-facing, generally sawtooth configuration around the circumference of the distal end of the sleeve. The configuration of these projections is such that the distal end of the sleeve will penetrate through opposing soft tissue without ripping or tearing the soft tissue when the sleeve is rotated in a first direction, and will cut through opposing bone in a saw-like manner when the sleeve is rotated in a second, opposite direction.

The driver means generally comprises an elongate driver having a longitudinal axis, a proximal end, a proximal portion adjacent the proximal end, a distal end, and a distal portion adjacent the distal end. The distal portion of the driver is adapted to drivingly engage the proximal end of the sleeve. The proximal portion of the driver is adapted to be drivingly engaged by a drill.

The suture anchor means and suture anchor installation tool means preferably comprise a suture anchor and a suture anchor installation tool of the type described and illustrated in U.S. Pat. application Ser. No. 07/902,513, which application has already been incorporated herein by reference. Attention is therefore directed to that application for a full and complete description of a suture anchor and suture anchor installation tool of the type preferably utilized in conjunction with this invention.

The foregoing system may be used to re-attach soft tissue to bone in the following manner.

First, the soft tissue is grasped (e.g. by forceps or a similar instrument) and then manipulated so that the tissue rests against the surface of the bone in its desired re-attachment position. Then the pin means is passed through the soft tissue and into the bone (e.g. by tapping or drilling) so that the pin's circumferential groove is aligned with the outer surface of the soft tissue. At this point the pin's pointed tip will extend sufficiently far into the bone to securely fix the pin (and hence the soft tissue) to the bone. Then, with the soft tissue pinned to the bone, the patient's anatomy may be manipulated about as necessary by the surgeon in order to determine if the soft tissue has been properly positioned relative to the bone. If the soft tissue is properly positioned relative to the bone, the surgeon moves forward to the next step in the procedure; if not, the pin is removed and the foregoing process repeated until the soft tissue has been pinned to the bone in the desired location.

Next, the sleeve means is slid telescopically over the proximal portion of the pin until the distal end of the sleeve touches the Outer surface of the soft tissue. Then the sleeve is manually pressed against the soft tissue and simultaneously rotated in the aforementioned first direction, so that the sleeve will make its way down to the top surface of the bone, without ripping or tearing the soft tissue. Next, the proximal portion of the driver means is loaded into an appropriate drill, and the distal end of the driver is drivingly engaged with the proximal end of the sleeve. Then the sleeve is rotated in its aforementioned second direction, so that the sawtoothed cutting means on the distal end of the sleeve cuts into the bone. The sleeve cuts downward in this manner, guided by the pin, until the sleeve's outer shoulder stops further penetration of the sleeve into the bone. At this point the sleeve's distal portion will extend sufficiently far into the bone to securely fix the sleeve to the bone. At the same time, a portion of the soft tissue will typically be captured between the sleeve's outer shoulder and the top surface of the bone, so as to effectively pin the soft tissue to the bone.

The driver is then disengaged from the proximal end of the sleeve. Next, the pin is completely withdrawn from the bone and the soft tissue. This leaves a hole in the bone where the pin was previously positioned. At the same time, the soft tissue is securely held in position against the bone by the sleeve, which extends through the soft tissue and into the bone.

A suture anchor is then passed down the interior of the sleeve using an appropriate installation tool. The suture anchor is forced downward into the hole left in the bone by the pin, until a shoulder located on the shaft of the installation tool engages the inner shoulder of the sleeve. At this point the suture anchor will reside at the proper depth in the bone.

Next the installation tool is withdrawn from the sleeve, leaving the suture anchor disposed in the bone and the suture anchor's associated suture extending out through the sleeve. The free ends of the suture are then tensioned slightly to ensure that the suture anchor is properly deployed in the bone. Once this has been done, the sleeve is withdrawn, leaving the free ends of the suture extending upwardly through the soft tissue. The free ends of the suture may then be used to secure the soft tissue to the bone.

By way of example, in a typical re-attachment procedure, three or more suture anchors may be used to attach one piece of soft tissue to a bone. In such a procedure, the soft tissue is first moved into position against the bone, in the manner discussed above. Then three or more pins are inserted through the soft tissue and into the bone. These pins secure the soft tissue to the bone, so that the surgeon may thereafter move the patient's anatomy through a range of motions to determine if the soft tissue is correctly positioned relative to the bone. If the soft tissue is not properly positioned, the pins are removed, the tissue is repositioned, etc. The foregoing procedure is repeated until the soft tissue has been stabilized in the desired position relative to the bone.

Once the surgeon is certain that the soft tissue has been properly positioned relative to the bone, the associated sleeves may be set, the various pins removed, the anchors deployed, and the sleeves removed, all in the manner previously described. Then the various free suture ends may be used to tie down the soft tissue to the bone.

BRIEF DESCRIPTION OF THE DRAWINGS

These and other objects and features of the present invention will be more fully disclosed or rendered obvious by the following detailed description of the preferred embodiment of the invention, which is to be considered together with the accompanying drawings wherein like numbers refer to like parts, and further wherein:

FIG. 2 is a side view of the sleeve means;

FIG. 3 is an end view of the distal end of the sleeve means;

FIG. 4 is a sectional view taken along line 4—4 of FIG. 2;

FIG. 7 is a side view of the driver means;

FIG. 8 is an end view of the distal end of the driver means;

FIG. 9 is an end view of the proximal end of the driver means;

FIGS. 11–20 show a series of steps involved in re-attaching soft tissue to bone in accordance with the present invention; and FIG. 21 shows the use of several suture anchors to re-attach soft tissue to bone in accordance with the present invention.

DETAILED DESCRIPTION OF THE PREFERRED EMBODIMENT

Figure 10:
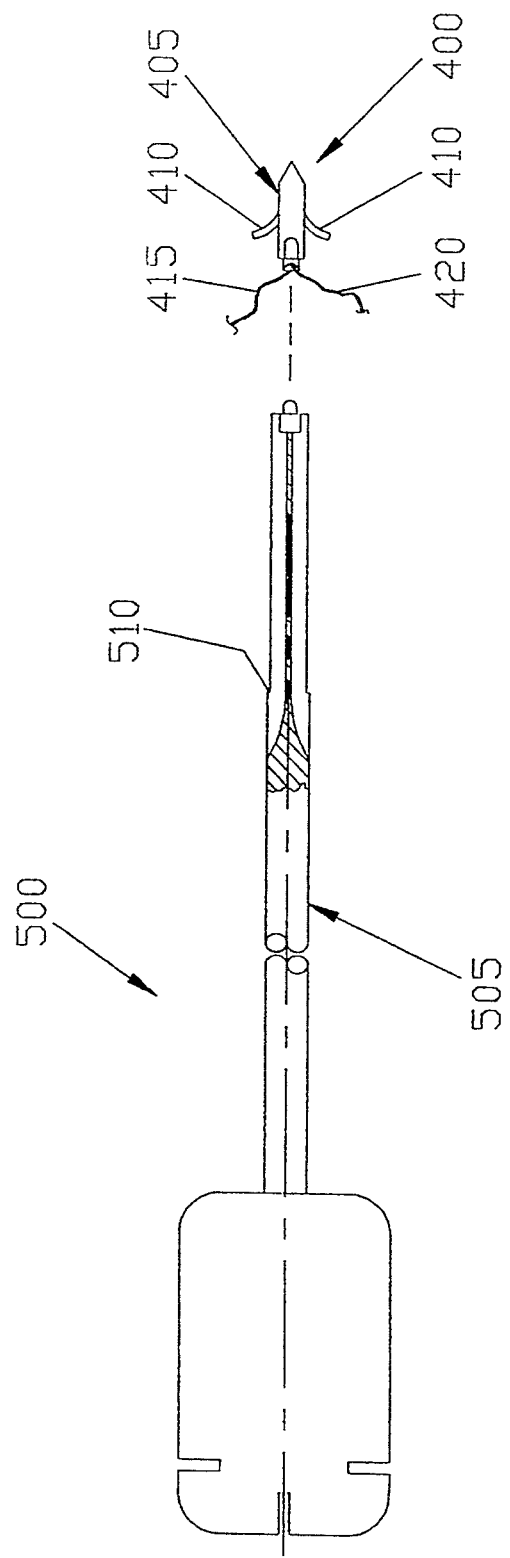
FIG. 10 is a side view of the suture anchor means and the suture anchor installation means.

Looking first at FIGS. 1, 2, 7 and 10, the preferred embodiment of the novel system for re-attaching soft tissue to bone generally comprises pin means 100 (FIG. 1), sleeve means 200 (FIG. 2), driver means 300 (FIG. 7), suture anchor means 400 (FIG. 10) and suture anchor installation tool means 500 (FIG. 10).

Figure 1:
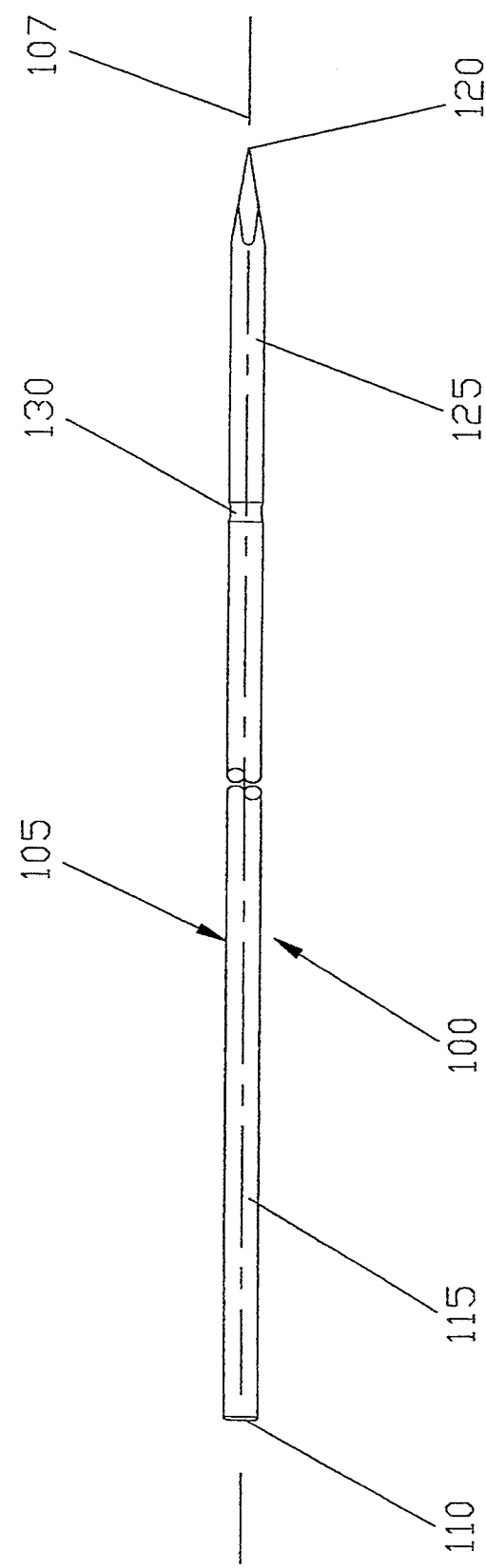
FIG. 1 is a side view of the pin means.

Looking now at FIG. 1, pin means 100 generally comprises an elongate, substantially rigid pin 105 having a longitudinal axis 107, a proximal end 110, a proximal portion 115 adjacent proximal end 110, a distal end 120, a distal portion 125 adjacent distal end 120, and a circumferential groove 130. Pin 105 has a substantially circular cross-section along most of its length. The distal portion of the pin tapers inwardly so as to form a sharp point at distal end 120. Circumferential groove 130 is located in a plane disposed perpendicular to the pin's longitudinal axis 107. Groove 130 is spaced a predetermined distance back from distal end 120, and separates the pin's proximal portion 115 from its distal portion 125.

Looking next at FIGS. 2-4, sleeve means 200 generally comprises an elongate sleeve 205 having a longitudinal axis 207, a proximal end 210, a proximal portion 215 adjacent proximal end 210, a distal end 220, and a distal portion 225 adjacent distal end 220. Sleeve 205 defines a central lumen 227 extending from its proximal end 210 to its distal end 220. The sleeve's proximal portion 215 has substantially square inner and outer cross-sections. The sleeve's distal portion 225 has substantially circular inner and outer cross-sections. The outer diameter of the sleeve's distal portion 225 is smaller than the outer diameter of the sleeve's proximal portion 215 (see FIGS. 2 and 3). Similarly, the inner diameter of the sleeve's distal portion 225 is smaller than the inner diameter of the sleeve's proximal portion 215. Accordingly, inner and outer shoulders 230 and 235, respectively, are formed where the distal portion of the sleeve joins the proximal portion of the sleeve (see FIG. 2).

Figure 5:
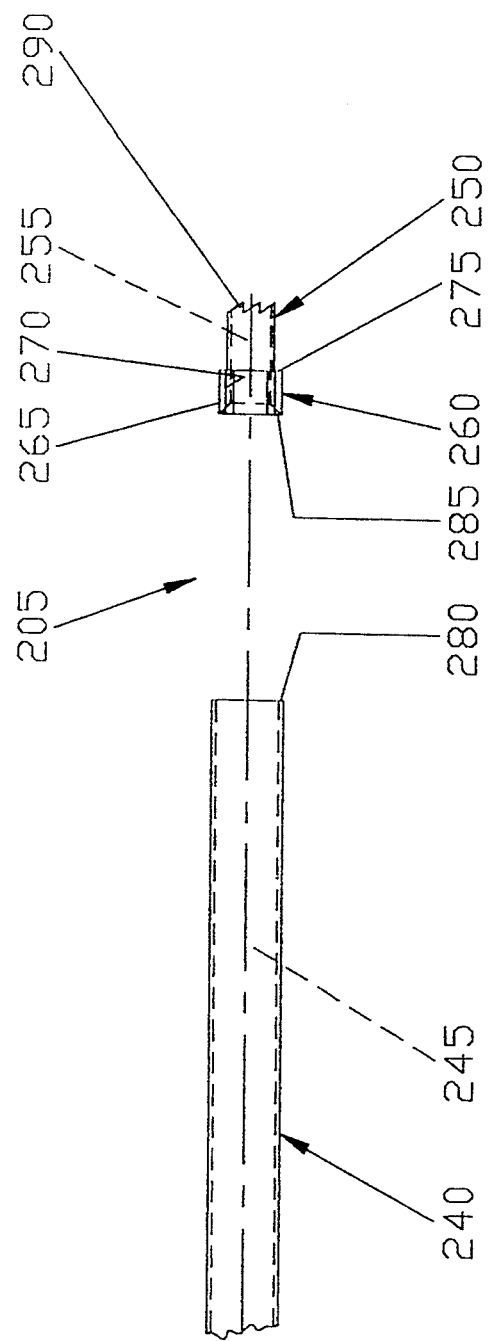
FIG. 5 is an enlarged, exploded view of selected portions of a preferred embodiment of the sleeve means.
Figure 6:
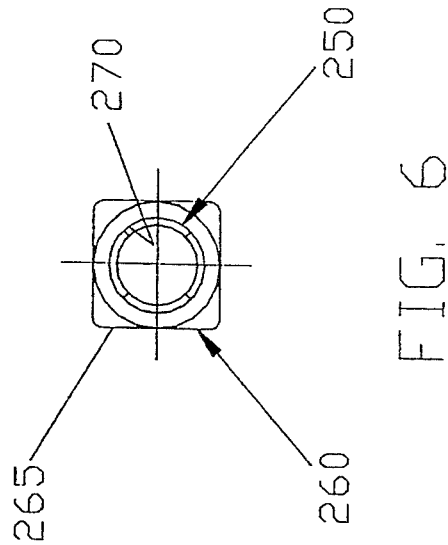
FIG. 6 is an enlarged end view of the distal end of the sleeve means shown in FIG. 5.

Sleeve 205 could be formed out of a single member if desired. More preferably, however, and looking now at FIGS. 5 and 6, sleeve 205 is formed out of a rectangular tube 240 having an internal passageway 245; a circular tube 250 having an internal passageway 255; and a connector 260 having a rectangular outer profile 265 and a circular inner profile 270. Rectangular tube 240, circular tube 250 and connector 260 are sized so that the proximal end of circular tube 250 can fit into, and be attached to, the circular interior of connector 250, with the distal end of circular tube 250 extending distally out of connector 260 in the manner shown (see FIG. 5). At the same time, connector 260 can fit into, and be attached to, the interior of rectangular tube 240 at the distal end of rectangular tube 240. Preferably connector 260 has its distal end surface 275 aligned with the tube's distal end surface 280, whereby the sleeve's outer shoulder 235 (FIG. 2) will be formed by the aligned surfaces 275 and 280. At the same time, the sleeve's interior shoulder 230 (FIG. 2) will be formed by the connector's proximal end surface 285.

The sleeve's distal end 220 is provided with an annular cutting surface. In the preferred embodiment, this cutting surface comprises a series of pointed, generally triangular projections 290 (see FIGS. 2 and 5). Projections 290 are arranged in a distally-facing, generally sawtooth configuration around the circumference of the distal end of the sleeve. The configuration of these projections is selected so that the distal end of the sleeve will penetrate through opposing soft tissue without ripping or tearing the tissue when the sleeve is rotated in a first direction, and will cut through opposing bone in a saw-like manner when the sleeve is rotated in a second, opposite direction. In this way sleeve 205 will be able to penetrate soft tissue cleanly and with minimum trauma when the sleeve is rotated in the aforementioned first direction; yet will be able to cut through hard bone efficiently when it is rotated in the aforementioned second direction. In the preferred embodiment, sleeve 205 will penetrate through opposing soft tissue without ripping or tearing the soft tissue when the sleeve is rotated in a counterclockwise direction, and will cut through opposing bone in a saw-like manner when it is rotated in a clockwise manner.

Looking next at FIGS. 7-9, driver means 300 comprises an elongate: driver 305 having a longitudinal axis 307, a proximal end 310, a proximal portion 315 adjacent proximal end 310, a distal end 320, and a distal portion 325 adjacent distal end 320. The driver's distal portion 325 is adapted to drivingly engage proximal end 215 of sleeve 205. In the preferred embodiment, this driving engagement is achieved by forming the driver's distal portion 325 with a square outer surface 330 (see FIGS. 7 and 8) which is sized to make a close sliding fit within the interior of the sleeve's proximal portion 215. In this way rotary motion may be transmitted between driver 305 and sleeve 205. The proximal portion 315 of driver 305 is adapted to be drivingly engaged by a standard surgical drill of the sort well known in the art. By way of example, the driver's proximal portion 315 is preferably formed with a round outer surface 335 (see FIGS. 7 and 9) whereby it may be easily connected to a standard drill chuck. Preferably the driver's proximal portion 315 has a larger outer diameter than the driver's distal portion 325, whereby an exterior shoulder 340 will be formed at the intersection of proximal portion 315 and distal portion 325. Shoulder 340 can act as a stop for engagement by the sleeve's proximal end 210 when the driver's distal portion 325 is being loaded into the interior of the sleeve's proximal portion 215.

Looking next at FIG. 10, suture anchor means 400 and suture anchor installation tool means 500 preferably comprise a suture anchor 405 and a suture anchor installation tool 505, wherein suture anchor 405 and suture anchor installation tool 505 are of the type described and illustrated in U.S. patent application Ser. No. 07/902,513, which application has already been incorporated herein by reference. Attention is therefore directed to that application for a full and complete description of the suture anchor 405 and the suture anchor installation tool 505. For the purposes of the present invention, it should be noted that suture anchor 405 includes a pair of diametrically opposed, outwardly extending, flexible barbs 410 for locking the suture anchor to a recipient bone as will hereinafter be discussed, and two free ends of suture 415 and 420 for use in re-attaching soft tissue to that bone, as will also hereinafter be discussed. It should also be noted that installation tool 505 includes an exterior shoulder 510 disposed part way down the length of its shaft.

The foregoing system may be used to re-attach soft tissue to bone in the following manner.

Figure 12:
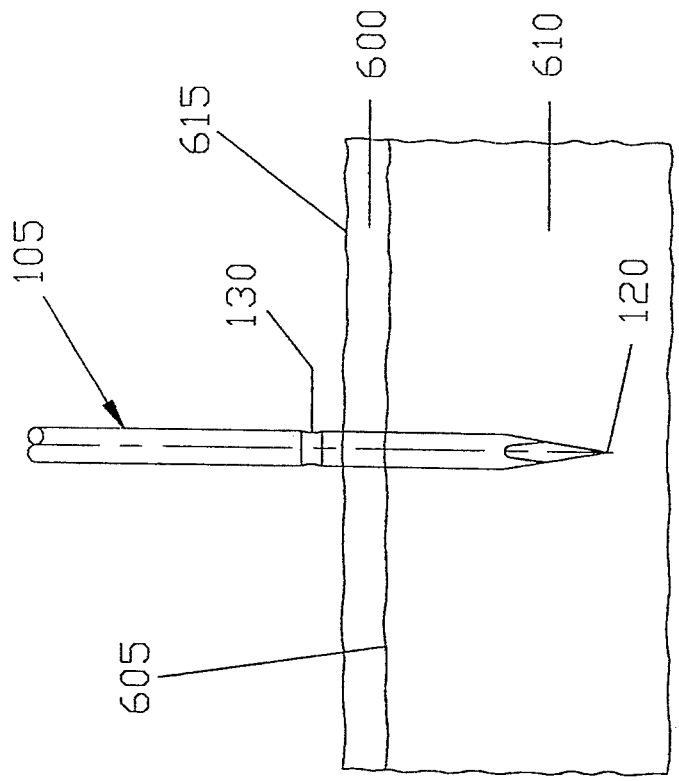
Figure 11:
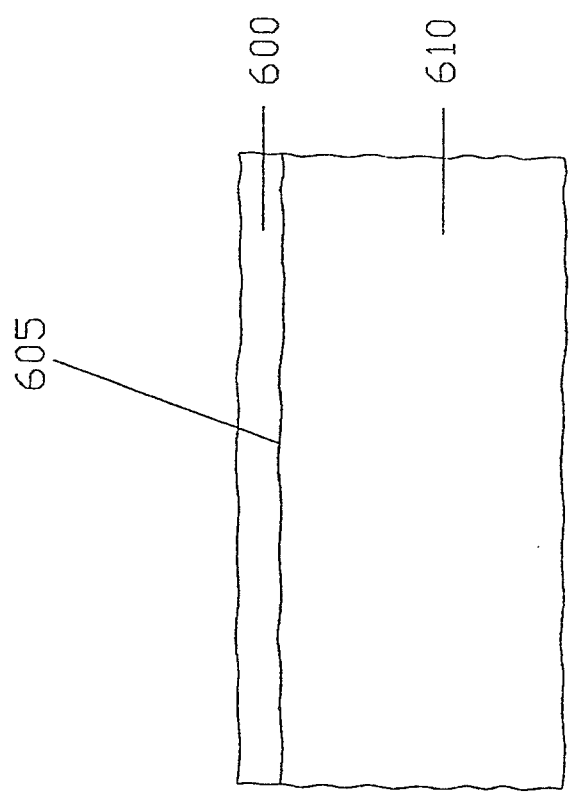

Looking first at FIG. 11, soft tissue 600 is grasped (e.g. by forceps or a similar instrument) and then manipulated so that tissue 600 rests in its desired re-attachment position against the top surface 605 of the bone 610. Then pin 105 is passed through soft tissue 600 and into bone 610 (e.g. by tapping or drilling) so that the pin's circumferential groove 130 is aligned with the outer surface 615 of soft tissue 600, in the manner shown in FIG. 12. At this point the pin's pointed tip 120 will extend sufficiently far into bone 610 to securely fix the pin (and hence soft tissue 600) to bone 610. In the typical procedure, pin 105 will extend all the way through the bone's hard outer cortical region, so that the pin's pointed tip 120 is located in the bone's softer inner cancellous region. Then, with soft tissue 600 pinned to bone 610, the patient's anatomy may be manipulated about as necessary by the surgeon in order to determine if soft tissue 600 has been properly positioned relative to bone 610. If soft tissue 600 is properly positioned relative to bone 610, the surgeon moves forward to the next step in the procedure; if not, pin 105 is removed and foregoing process repeated until soft tissue 605 has been pinned to bone 610 in the desired location.

Figure 14:
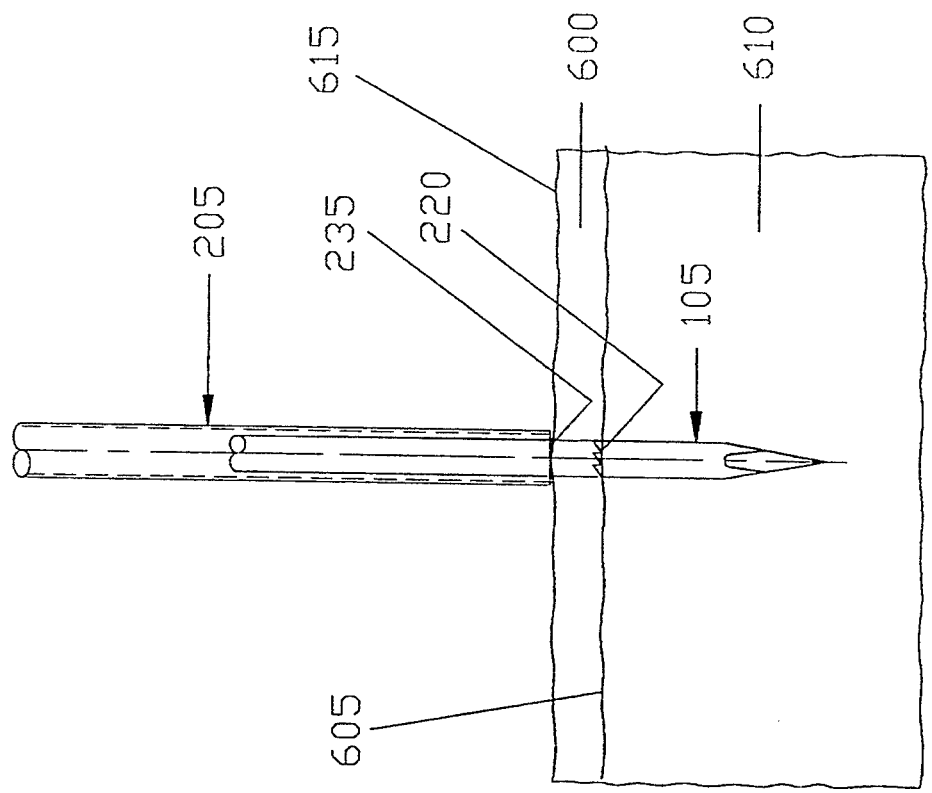
Figure 13:
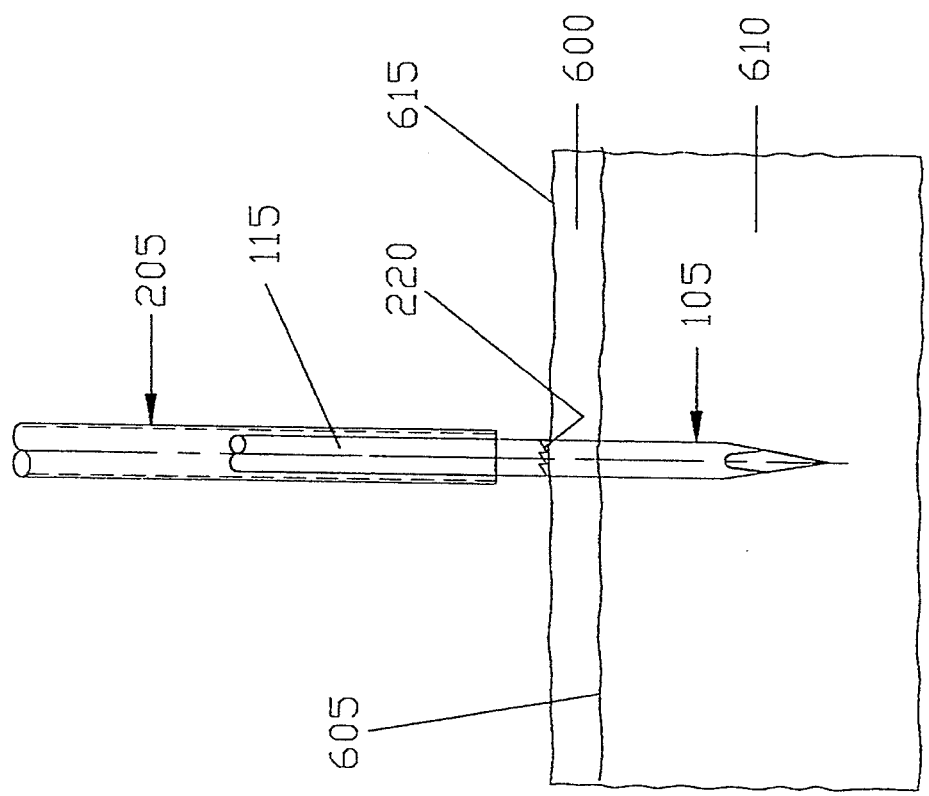
Figure 15:
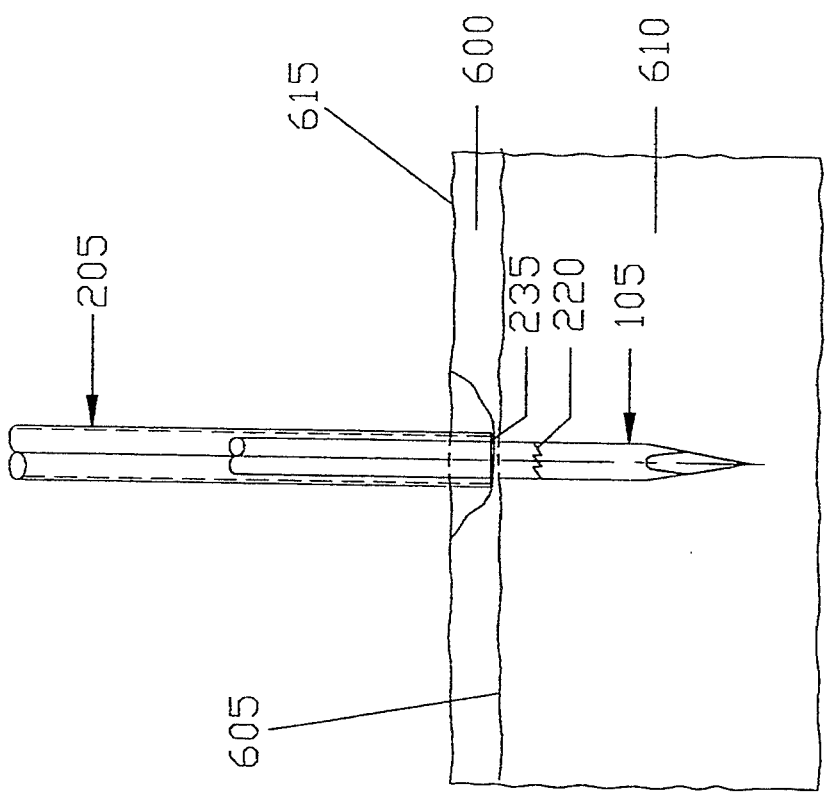

Next, sleeve 205 is slid telescopically over the proximal portion 115 of the pin until the sleeve's distal end 220 touches outer surface 615 of soft tissue 600, in the manner shown in FIG. 13. Then sleeve 205 is manually pressed against soft tissue 600, and simultaneously rotated in the aforementioned first direction, so that sleeve 205 will make its way cleanly down to the top surface 605 of bone 610, without ripping or tearing the soft tissue. See FIG. 14. At this point the sleeve's exterior shoulder 235 may or may not be engaging the top surface 615 of tissue 600, depending on the thickness of soft tissue 600. Next, the proximal portion 315 of driver 305 is loaded into an appropriate drill, and the distal end 325 of driver 305 is drivingly inserted into the proximal end 215 of sleeve 205, so as to drivingly connect sleeve 205 to the drill. Then sleeve means 205 is rotated in its aforementioned second direction, so that the sawtoothed cutting means on the distal end 220 of the sleeve cuts into bone 610. Sleeve 205 cuts downward, guided by pin 105, until the sleeve's outer shoulder 235 stops further penetration of sleeve into the bone. At this point the sleeve's distal portion 225 will extend sufficiently far into bone 610 to securely fix sleeve 205 to bone 610. At the same time, a portion of soft tissue 600 will typically be captured between the sleeve's outer shoulder 235 and the bone's top surface 605, thereby effectively pinning the soft tissue to the bone. See FIG. 15.

Figure 16:
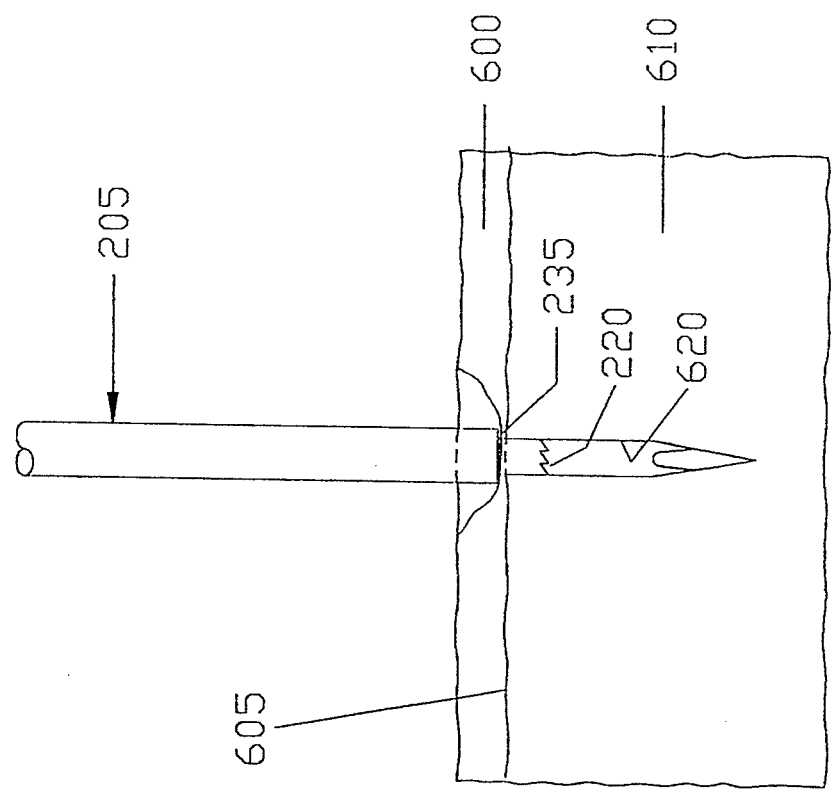

Driver 305 is then disengaged from the sleeve's proximal end 215. Next, pin 105 is completely withdrawn from bone 610 and soft tissue 600. This leaves a hole 620 in bone 610 where pin 105 was previously positioned. At the same time, soft tissue 600 is securely held in position against bone 610 by sleeve 205, which extends through soft tissue 600 and into bone 610. See FIG. 16.

A suture anchor 405 is then passed down the interior lumen 227 of sleeve 205 using an appropriate installation tool 505. Suture anchor 405 and sleeve 205 are sized relative to one another such that the suture anchor's barbs 410 will lightly engage and ride along the inside surfaces of the sleeve's proximal portion 215, until the anchor's barbs solidly engage and are deflected inwardly and rearwardly by the sleeve's inner shoulder 230. Suture anchor 405 is forced through the sleeve's distal portion 225 and then downward into the hole 620 left in bone 610 by pin 105, until the installation tool's shoulder 510 engages the inner shoulder 230 of sleeve 205. At this point suture anchor 405 will reside at the proper depth in bone 610, with the anchor's barbs 410 solidly engaging bone 610. See FIG. 17.

Next, installation tool 505 is withdrawn from sleeve 205, leaving suture anchor 405 disposed in bone 610, with the suture anchor's associated suture ends 415 and 420 extending out through sleeve 205. See FIG. 18. The free suture ends 415 and 420 are then tensioned slightly to ensure that the suture anchor is properly seated in the bone, with its barbs 410 fully deployed. Once this has been done, sleeve 205 is withdrawn, leaving the free ends of the suture extending upwardly through soft tissue 600. See FIG. 19. The free ends of the suture may then be used to secure soft tissue 600 to bone 610. By way of simple example, suture ends 415 and 420 are shown in FIG. 20 holding a washer 625 tightly against the soft tissue's top surface 615, whereby soft tissue 600 is securely fastened to bone 600.

By way of further example, and looking now at FIG. 21, in a typical re-attachment procedure, three or more suture anchors 405A, 405B, 405C, etc. may be used to attach one piece of soft tissue 600 to bone 610. In such a procedure, soft tissue 600 is first moved into position against bone 610, in the manner previously discussed. Then three or more pins 105 are inserted through the soft tissue and into the bone. These pins secure soft tissue 600 to bone 610, so that the surgeon may thereafter move the patient's anatomy through a range of motions to determine if the soft tissue is correctly positioned against the bone. If the soft tissue is not properly positioned, the pins are removed, the tissue is repositioned, etc. The foregoing procedure is repeated until soft tissue 600 has been stabilized in the desired position relative to bone 610.

Once the surgeon is certain that the soft tissue has been properly positioned against the bone, the associated sleeves 205 may be set, the various pins 105 removed, the anchors 405A, 405B, 405C, etc. deployed and the sleeves 205 removed, all in the manner previously described. Then the free suture ends may be used to tie down the soft tissue to the bone. For example, suture end 415A of suture anchor 405A can be tied to suture end 420B of suture anchor 405B; suture end 415B of suture anchor 405B can be tied to suture end 420C of suture anchor 405C; etc. Alternatively, if desired, one of the sleeves 205 may be left in the bone to hold the soft tissue steady while several adjacent sutures are tied off, and then that sleeve may be removed to allow its own sutures to be tied off. Thus, in the example of FIG. 21, the sleeve 205 associated with suture anchor 405C might be left engaging bone 610 while suture ends 415A and 420B are tied off, and then that sleeve removed to allow suture ends 415B and 420C to be tied off, etc.

It should be appreciated that the system and method of the present invention may be used in both open surgical procedures and so-called closed surgical procedures to re-attach soft tissue to bone. In a closed surgical procedure, e.g. an arthroscopic or endoscopic surgical procedure, each of the pins 105 (and their associated sleeves 205, suture anchors 405, etc.) would typically be passed down to the surgical site via separate cannulas, in ways well known in the art.

It should also be appreciated that numerous modifications may be made to the foregoing apparatus and method without departing from the scope of the present invention.

Thus, for example, one might practice the present invention using suture anchors and suture anchor installation tools other than those of the sort disclosed in U.S. patent application Ser. No. 07/902,513.

Furthermore, while in the foregoing description the present invention has been discussed in the context of re-attaching soft tissue to bone, it should be appreciated that the invention might also be used to attach prosthetic devices and/or grafts of natural or synthetic materials to bone or bone-like structures.

These and other changes of their type are considered to be within the scope of the present invention.

Advantages Of The Invention

Numerous advantages are obtained by using the present invention.

For one thing, a novel system and method is provided for re-attaching soft tissue to bone, which improves upon the deficiencies of the prior art devices and techniques previously discussed.

The present invention also provides a novel system and method for re-attaching soft tissue to bone, wherein suture anchors do not need to be deployed in the bone until after the soft tissue has been securely attached to the bone and its optimum placement confirmed.

The present invention also allows the surgeon to determine the optimum location for tissue re-attachment prior to anchoring any connective suture to the bone.

And the present invention provides a novel system and method for re-attaching soft tissue to bone which avoids irretrievably deploying suture anchors in the bone at locations other than the optimum locations for tissue re-attachment.

Another advantage of the invention is that it provides a novel system and method for re-attaching soft tissue to bone which is easy to use and perform.

The present invention also provides a novel system and method for re-attaching soft tissue to bone which expedites and facilitates the re-attachment procedure.

Another advantage of the invention is that it minimizes trauma to the patient during the tissue re-attachment procedure.

And the present invention is usable in the attachment of prosthetic devices and/or grafts of natural and/or synthetic material to bone or bone-like structures.

Also the present invention may be used to re-attach soft tissue to bone in both open surgical procedures and in closed surgical procedures (e.g. arthroscopic or endoscopic surgical procedures).

What is claimed is:

1. A system for use in attaching an object to bone, said system comprising:
   pin means for pinning said object to bone and sleeve means for mounting on said pin means;
   said pin means being adapted to penetrate through said object and into said bone to a desired depth, said pin means comprising an elongate, rigid pin having a first longitudinal axis, a first outer surface, a distal end, a distal portion adjacent said distal end, a proximal end, a proximal portion adjacent said proximal end, and marker means located on said outer surface of said pin for providing a visual reference indicative of the depth of penetration of said distal end through said object and into said bone, said distal end defining a pointed tip;

said sleeve means comprising an elongate, tubular sleeve having an inner surface, an outer surface, a distal end, a distal portion adjacent said distal end, a proximal end, and a proximal portion adjacent said proximal end;

the inner surface of said proximal portion of said sleeve defining an internal, longitudinally-extending first lumen, said first lumen being further defined by internal longitudinal walls, each said wall having a pair of opposing longitudinally extending side edges and being joined at an angle to adjacent ones of said walls along one or the other of said side edges;

the inner surface of said distal portion of said sleeve defining an internal, longitudinally-extending second lumen having a substantially circular cross-section;

said proximal portion of said sleeve and said distal portion of said sleeve being joined together end to end such that said first and second lumens define a passageway centered on said longitudinal axis of said sleeve, with said passageway being sized to receive said pin, and said passageway extending from said proximal end of said sleeve to said distal end of said sleeve, and such that an internal, proximally-facing shoulder and an external, distally-facing shoulder are formed in the inner and outer surfaces of said sleeve, respectively, at the point where said proximal portion of said sleeve joins said distal portion of said sleeve;

said distal portion of said sleeve having a longitudinal length substantially shorter than the longitudinal length of said proximal portion of said sleeve; and said distal end of said sleeve defining distally facing cutting means for cutting through said object and bone.

2. A system according to claim 1 wherein said cutting means comprises a series of cutting teeth extending from said distal end of said sleeve.

3. A system according to claim 2 wherein said cutting means are adapted to cleanly penetrate soft tissue without ripping or tearing said tissue when said sleeve is rotated in one direction about its said longitudinal axis, and to cut through bone when said sleeve is rotated in the other direction about its said longitudinal axis.

4. A system according to claim 1 wherein the axial length of said pin means is selected to be substantially longer than the axial length of said sleeve.

5. A system according to claim 1 further comprising driver means for driving said sleeve and driver rotation means for rotating said driver means;

said driver means comprising a short tubular driver having a longitudinal axis, a proximal end, a proximal portion adjacent said proximal end, a distal end, and a distal portion adjacent said distal end;

said distal portion of said driver having a cross-section corresponding to, but slightly smaller than, said cross-section of said lumen of said proximal portion of said sleeve such that said distal portion of said driver may be longitudinally inserted into said proximal portion of said sleeve in abutting relation with said side walls;

said proximal portion of said driver having a substantially circular cross-section and being adapted to be grasped by said driver rotation means; and said proximal portion of said driver and said distal portion of said driver being joined end to end so as to form a distally facing shoulder on the outer surface of said driver adapted to engage said proximal end of said sleeve when said distal portion of said driver is loaded into said proximal portion of said sleeve.

6. A system according to claim 5 wherein said driver rotation means comprises a drill.

7. A system according to claim 1 further comprising a suture anchor having an attached length of suture, and a suture anchor installation tool;

said suture anchor comprising a coupling member and at least one barb;

said coupling member having a longitudinal axis and including means for attaching a portion of said length of suture thereto;

said at least one barb normally extending longitudinally and radially from said coupling member to an outer end located outwardly of an axial projection of the maximum cross-section of the coupling member, but being elastically deformable into a configuration located within said axial projection; and said suture anchor insertion tool having a distal end adapted to releasably grasp said anchor and defining a distally facing shoulder located at a preselected distance from said distal end of said tool exceeding the longitudinal length of said distal portion of said sleeve by at least a length equal to the longitudinal length of said anchor, said installation tool shaft being adapted for insertion into and along said passageway in said sleeve from said proximal end of said sleeve until said distally facing tool shoulder engages said proximally facing shoulder on the inner surface of said sleeve.

8. A method for re-attaching soft tissue to bone, said method comprising the steps of:
(1) providing:
   a pin;
   a sleeve;
   a suture anchor including an associated length of suture; and
   a suture anchor installation tool;
(2) placing the soft tissue against the bone in its desired re-attachment position;
(3) passing said pin through said soft tissue and into said bone so as to securely fix said pin and said soft tissue to said bone;
(4) manipulating the patient's anatomy as needed to determine if said soft tissue has been properly positioned relative to said bone and, if said soft tissue has not been properly positioned, removing said pin from said bone and said soft tissue, repositioning said soft tissue against said bone, and returning to Step 3 above;
(5) passing said sleeve telescopically over said pin, through said soft tissue and partially into said bone so as to securely fix said sleeve to said bone;
(6) withdrawing said pin from said bone and said soft tissue;

(7) passing the suture anchor down the interior of said sleeve and into said bone, using the suture anchor installation tool;
(8) withdrawing said suture anchor installation tool, leaving said suture anchor deployed in the bone and its associated suture extending out through said sleeve;
(9) withdrawing said sleeve; and
(10) using the free ends of the suture to secure said soft tissue to said bone.

9. A method for re-attaching soft tissue to bone, said method comprising the steps of:
(1) providing:
pin means;
sleeve means;
suture anchor means including an associated length of suture; and
suture anchor installation tool means;
(2) placing the soft tissue against the bone in its desired re-attachment position;
(3) passing said pin means through said soft tissue and into said bone so as to securely fix said pin means and said soft tissue to said bone;
(4) manipulating the patient's anatomy as needed to determine if said soft tissue has been properly positioned relative to said bone and, if said soft tissue has not been properly positioned, removing said pin means from said bone and said soft tissue, repositioning said soft tissue against said bone, and returning to Step 3 above;
(5) passing said sleeve means telescopically over said pin means, through said soft tissue and partially into said bone so as to securely fix said sleeve means to said bone;
(6) withdrawing said pin means from said bone and said soft tissue;
(7) passing the suture anchor means down the interior of said sleeve means and into said bone, using the suture anchor installation tool means;
(8) withdrawing said suture anchor installation tool means, leaving said suture anchor means deployed in the bone and its associated suture extending out through said sleeve means;
(9) withdrawing said sleeve means; and
(10) using the free ends of the suture to secure said soft tissue to said bone.

* * * * *